United States Patent [19]

DePriest

[11] Patent Number: 4,611,071

[45] Date of Patent: Sep. 9, 1986

[54] METAL ALKYL PROCESS

[75] Inventor: Robert N. DePriest, Baton Rouge, La.

[73] Assignee: Ethyl Corporation, Richmond, Va.

[21] Appl. No.: 701,292

[22] Filed: Feb. 13, 1985

[51] Int. Cl.$^4$ .......................... C07F 9/72; C07F 9/90; C07F 9/94

[52] U.S. Cl. ...................... 556/70; 556/121; 556/96; 556/1; 556/187; 568/8

[58] Field of Search .......................................... 556/70

[56] References Cited

U.S. PATENT DOCUMENTS

| | | | |
|---|---|---|---|
| 2,012,356 | 8/1935 | Shappirio | 556/70 |
| 2,838,508 | 6/1958 | Ramsden | 260/665 G X |
| 2,912,465 | 11/1959 | Ramsden | 568/8 |
| 2,915,566 | 12/1959 | Normant et al. | 260/665 G |
| 2,943,115 | 6/1960 | Normant et al. | 260/665 G |
| 2,959,596 | 11/1960 | Ramsden | 556/70 |
| 3,083,242 | 3/1963 | Ramsden | 260/665 G |
| 3,099,690 | 7/1963 | Rauhut et al. | 568/8 |

FOREIGN PATENT DOCUMENTS

| | | | |
|---|---|---|---|
| 883873 | 10/1971 | Canada | 568/8 |
| 924773 | 5/1963 | United Kingdom | 260/665 G |

OTHER PUBLICATIONS

Doak et al, Organometallic Compounds of Arsenic, Antimony and Bismuth, John Wiley & Sons, N.Y., pp. 127–132, 361–366, 419–423 (1970).

Primary Examiner—Helen M. S. Sneed
Attorney, Agent, or Firm—Donald L. Johnson; John F. Sieberth; Joseph D. Odenweller

[57] ABSTRACT

Metal alkyls such as trimethyl arsine are made in improved yields by reacting a metal halide, e.g. AsCl$_3$, with a Grignard reagent such as methyl magnesium bromide complexed with a polyether such as di(2-methoxyethyl)ether.

27 Claims, No Drawings

METAL ALKYL PROCESS

BACKGROUND OF THE INVENTION

Metal alkyls are valuable compounds finding extensive use in organic synthesis. They can also be used as a source of pure metal by thermo decomposition of the purified metal alkyl. For example, mixtures of gallium and arsenic alkyls can be thermally decomposed to form a gallium-arsenide alloy which in highly purified form can be used as an efficient semi-conductor.

Metal alkyls such as arsenic alkyls have been made by the reaction of aluminum alkyls with arsenic trihalides (British Pat. No. 768,765 and British Pat. No. 820,146). Trimethyl arsine has been made by the reaction of methyl magnesium iodide with arsenic trichloride (Efremov et al. "Tr. Khim. Tekhnol." 1975 (1) 3-4). A similar preparation can be made using arsenic tribromide (Berichte 39 160 (1906)). Ayscough et al. "J. Chem. Soc." 3381 (1954) report the synthesis of trimethyl arsine by reacting arsenic trichloride with methyl magnesium iodide in di-n-butyl ether.

One problem encountered in the prior methods using Grignard reagent is that the metal alkyls, especially the Group VA metal alkyls, are strong bases and coordinate with the acidic metal halides (e.g. magnesium chloride) in the reaction system making recovery difficult. This generally requires hydrolysis to remove the metal halide.

Accordingly, a need exists for an efficient method for making metal alkyls using a Grignard reagent which does not lead to complex formation of the metal alkyl with the magnesium halide by-product.

SUMMARY OF THE INVENTION

According to the present invention, metal alkyls, especially Group VA metal alkyls such as trialkyl arsines can be made in high yield without encountering a complex of the metal alkyl with magnesium halide by forming a complex between the Grignard reagent and a polyether and reacting this complex with a metal halide to form the metal alkyl which can be recovered in high yield without hydrolysis by distillation.

DESCRIPTION OF THE PREFERRED EMBODIMENTS

A preferred embodiment of the invention is a process for making metal alkyls, said process comprising reacting a halide of a metal capable of forming a metal alkyl with a hydrocarbyl magnesium halide Grignard-polyether complex in an inert ether reaction medium in which the metal alkyl product is soluble.

The process can be applied to any metal halide capable of forming a metal alkyl. These include zinc, cadmium, mercury, aluminum, gallium, silicon, germanium, tin, lead, phosphorus, arsenic, antimony, bismuth and the like. The process is most useful with the halides of metals in Group VA which includes $PCl_3$, $PBr_3$, $AsCl_3$, $AsBr_3$, $AsI_3$, $SbCl_3$, $SbBr_3$, $SbI_3$, $BiCl_3$, $BiBr_3$ and $BiI_3$. The Group VA metals present a particular problem because the alkyls are quite basic and form a complex with magnesium halides which are by-products in the process. This makes recovery very difficult. The complex must be hydrolyzed or subject to thermal cracking or treated with a stronger base prior to recovery of product. In any event, the yield is substantially decreased.

The process is readily conducted by first forming a complex between the Grignard reagent and a polyether. Suitable Grignard reagents include any of the hydrocarbyl magnesium halides, both aromatic and aliphatic. Examples of suitable Grignards are phenyl magnesium chloride, phenyl magnesium bromide, phenyl magnesium iodide, tolyl magnesium bromide, naphthyl magnesium iodide, methyl magnesium chloride, methyl magnesium bromide, methyl magnesium iodide, ethyl magnesium bromide, ethyl magnesium chloride, isobutyl magnesium chloride, 2-ethylhexyl magnesium chloride, n-dodecyl magnesium bromide, cyclohexyl magnesium chloride, cycloheptyl magnesium iodide, cyclooctyl magnesium bromide and the like. Grignard reagents made by reacting magnesium metal with primary alkyl halides containing 1 to about 12 carbon atoms are more preferred. Examples of these are methyl magnesium chloride, ethyl magnesium bromide, n-propyl magnesium iodide, n-butyl magnesium chloride, n-pentyl magnesium iodide, isobutyl magnesium bromide, isopentyl magnesium chloride, 2-ethylhexyl magnesium iodide, n-octyl magnesium chloride, n-decyl magnesium bromide, 2-ethyloctyl magnesium iodide, n-dodecyl magnesium iodide, 2-ethyldecyl magnesium bromide and the like.

The Grignard can be made in any suitable inert ether reaction medium such as diethyl ether, dipropyl ether, ethylpropyl ether, di-n-butyl ether, ethyl n-butyl ether, tetrahydrofuran, methyl n-butyl ether, methyl n-hexyl ether, and the like. Di-n-butyl ether has been used with excellent results.

The methods of making Grignard reagents are well-known. The ether must be dry. Magnesium turnings or chips are placed in the dry ether under nitrogen and a small amount of hydrocarbyl halide added generally at room temperature. The mixture is stirred until the reaction initiates. Addition of a small amount of previously made Grignard can shorten the initiation period. After initiation, the remaining hydrocarbyl halides can be slowly added at temperatures up to reflux but generally at about 20°-30° C. An excess of magnesium is generally used. The ether solution containing the Grignard can then be decanted from the unreacted magnesium which can be used for subsequent Grignard preparations.

The ether solution of Grignard reagents is placed in a reaction vessel under nitrogen and converted to an insoluble complex by addition of a polyether. Suitable polyethers include di(2-methoxyethyl)ether, di(2-ethoxyethyl)ether, dioxane, dimethoxy ethane, diethoxy ethane and the like.

The most preferred polyethers are the di-$C_{1-4}$ alkyl ethers of polyalkylene glycols, especially polyethylene glycols and polypropylene glycols or mixed polyethylene-propylene glycols. Some examples of these polyethers are the dimethyl ether of diethylene glycol, diethyl ether of diethylene glycol, di-n-butyl ether of diethylene glycol, dimethyl ether of triethylene glycol, diethyl ether of triethylene glycol, di-n-butyl ether of triethylene glycol, dimethyl ether of dipropylene glycol, diethyl ether of dipropylene glycol, di-n-butyl ether of dipropylene glycol, and the like.

The polyether should be dried by standard methods such as by storing over metallic sodium. The dried polyether is then slowly added to the stirred ether Grignard solution under nitrogen. Temperature is not critical and can be from below room temperature (e.g. 0° C.) up to the reflux temperature of the inert ether. Good results are achieved at room temperature. The amount of polyether should be about 1 mole per mole of Grignard reagent. A suitable range is about 0.9–1.5 moles of polyether per mole of hydrocarbyl magnesium halide. A greater excess can be used but is not required.

The polyether complexes with the Grignard reagent to form an insoluble heavy white suspension. If the slurry becomes too thick, additional inert ether reaction medium can be added. The amount of inert ether should be an amount that will maintain a stirrable slurry.

The dry metal halide is then added in small increments under an inert atmosphere at temperatures from about 0° C. up to reflux or higher when operating under pressure. The addition is usually started at room temperature and the temperature allowed to rise to about 50°–70° C. or to the reflux temperature of the inert ether reaction medium. Depending on the scale of the reaction, the addition is usually complete in from 1 minute up to several hours. After completion of the metal halide addition, the mixture is preferably stirred for a period (e.g. 0.5–2 hours) to make sure the reaction has proceeded to completion. Product can then be recovered by distillation of the reaction mixture. The preferred inert ether reaction medium has a boiling point above the boiling point of the metal alkyl product. It can then act as a chaser in the distillation. If the inert ether used has a boiling point below the boiling point of the metal alkyl product, then an inert chaser should be added. This can be a higher boiling ether or any high boiling inert hydrocarbon. Use of an inert ether reaction medium boiling close to the metal alkyl product should be avoided because this can make separation very difficult.

The following examples serve to illustrate how the process is conducted and its advantages over the prior methods.

EXAMPLE 1

A reaction vessel was fitted with a stirrer, dropping funnel and a 6-inch packed distillation head. The vessel was purged with nitrogen and then charged with 165.5 grams of a 25.5 weight percent solution of methyl magnesium bromide in di-n-butyl ether (0.354 moles). An additional 103 grams of di-n-butyl ether was added and then 60 ml (0.43 moles) of di(2-methoxyethyl)ether over a 3 minute period while stirring. The temperature rose from 25° to 42° C. and a heavy white suspension formed. An additional 20 ml of di-n-butyl ether was added to improve stirring. Then 8.7 ml (0.1 moles) of arsenic trichloride was added dropwise over a 30 minute period. Temperature rose from 42° up to 72°. The dropping funnel was rinsed into the reaction vessel with 20 ml of di-n-butyl ether. The reaction mixture was stirred 1 hour while being heated from 25° to 130° C. using an oil bath and the product was distilled upon further heating. The distillate, collected over the range 48°–125° C., contained 9.66 grams of trimethylarsenic (80% yield from arsenic trichloride) and 2.36 grams of di-n-butyl ether. The distillate was then fractionally distilled to give 7.20 grams (60% yield from arsenic trichloride) of 99+% pure trimethylarsenic (boiling range 51.9° to 52.4° C.).

EXAMPLE 2

This is a comparative example showing the results obtained in the same reaction without the use of the Grignard-polyether complex.

In a reaction vessel provided with a nitrogen atmosphere was placed 126 grams of a 28.08 weight percent solution of methyl magnesium bromide in di-n-butyl ether (0.297 moles). To this was added using a dropping funnel 7.0 grams (0.085 moles) of $AsCl_3$ over a 10 minute period with vigorous stirring and external ($-50°$ to $-60°$ C.) cooling. The mixture was then allowed to warm to room temperature forming a pasty solid. An additional 25 ml of di-butyl ether and 60 ml of dry xylene was added. This was stirred 2 hours at room temperature and then cooled to 0° C. Then 60 ml of water was added carefully and slowly giving a slight exotherm. Phases were allowed to separate overnight. Organic phase was clear reddish color but aqueous phase was thick pasty mass. Added 60 ml saturated $NH_4Cl$ solution and stirred. Let settle and siphon off organic phase. The organic phase was distilled through 6 inch Vigreaux column to obtain about 30 ml of cloudy distillate. It was dried with 0.5 grams of molecular sieves. It was then re-distilled to obtain a fraction at 48.8°–49.2° C. (5.47 grams) of trimethyl arsine, 54% yield.

EXAMPLE 3

This is another comparative example showing the results without hydrolysis.

A reaction vessel under nitrogen was charged with 132.18 grams of 28.1 weight percent methyl magnesium bromide (0.312 moles). Then 7.0 ml (0.084 moles) of $AsCl_3$ was added dropwise over 20 minutes at $-5°$ C. to 0° C. The mixture was stirred 45 minutes at room temperature and then 40 ml of di-butyl ether was added. It was then attempted to distill the mixture by heating in an oil bath to 145° C. and then 160° C. No distillate formed. The mixture was cooled to room temperature and hydrolyzed by addition of 60 ml of saturated aqueous $NH_4Cl$. Then 60 ml di-butyl ether was added and stirred. The phases were allowed to separate and the ether phase decanted off and dried over 5 grams calcium chloride. It was then distilled to obtain 4.3 grams trimethyl arsine (b.p. 48.2–48.5), a 42% yield.

These results show a significant yield improvement and much simpler procedure due to the use of the present process.

I claim:

1. A process for making Group VA metal alkyls, said process comprising reacting a halide of a Group VA metal with a hydrocarbyl magnesium halide Grignard reagent—polyether complex in an inert ether reaction medium in which the Group VA metal alkyl product is soluble.

2. A process of claim 1 wherein said metal halide is a arsenic trihalide halide.

3. A process of claim 2 wherein said polyether is dioxane.

4. A process of claim 2 wherein said polyether is a di-$C_{1-4}$ alkoxy ethane.

5. A process of claim 4 wherein said polyether is di-methoxyethane.

6. A process of claim 2 wherein said polyether is a di-$C_{1-4}$ alkyl ether of a polyalkylene glycol.

7. A process of claim 6 wherein said polyether is a di-$C_{1-4}$ alkyl ether of diethylene glycol.

8. A process of claim 7 wherein said polyether is the dimethyl ether of diethylene glycol.

9. A process of claim 2 wherein said Grignard reagent is a $C_{1-12}$ alkyl magnesium halide.

10. A process of claim 9 wherein said Grignard reagent is a $C_{1-12}$ alkyl magnesium bromide.

11. A process of claim 9 wherein said Grignard reagent is a methyl magnesium halide.

12. A process of claim 11 wherein said Grignard is methyl magnesium bromide.

13. A process of claim 2 wherein said arsenic trihalide is arsenic trichloride.

14. A process of claim 2 wherein said Grignard reagent is a $C_{1-12}$ alkyl magnesium halide.

15. A process of claim 14 wherein said polyether is a di-$C_{1-4}$ alkyl ether of a polyalkylene glycol.

16. A process of claim 15 wherein said polyether is a di-$C_{1-4}$ alkyl ether of diethylene glycol.

17. A process of claim 15 wherein said polyether is the dimethyl ether of diethylene glycol.

18. A process of claim 16 wherein said Grignard reagent is a methyl magnesium halide.

19. A process of claim 18 wherein said Grignard reagent is methyl magnesium bromide.

20. A process of claim 17 wherein said Grignard reagent is a methyl magnesium halide.

21. A process of claim 20 wherein said Grignard reagent is methyl magnesium bromide.

22. A process of claim 14 wherein said inert ether reaction medium is a di-$C_{2-6}$ alkyl ether.

23. A process of claim 22 wherein said polyether is a di-$C_{1-4}$ alkyl ether of a polyalkylene glycol.

24. A process of claim 23 wherein said polyether is the dimethyl ether of diethylene glycol.

25. A process of claim 24 wherein said arsenic trihalide is arsenic trichloride.

26. A process of claim 25 wherein said Grignard reagent is methyl magnesium bromide.

27. A process of claim 26 wherein said inert ether reaction medium is di-n-butyl ether.

* * * * *